(12) United States Patent
Oguchi

(10) Patent No.: US 8,292,622 B2
(45) Date of Patent: Oct. 23, 2012

(54) IMPLANT METHOD

(75) Inventor: Hiroshi Oguchi, Gifu (JP)

(73) Assignee: International Aesthetic Implant Center, Gifu (JP)

( * ) Notice: Subject to any disclaimer, the term of this patent is extended or adjusted under 35 U.S.C. 154(b) by 146 days.

(21) Appl. No.: 12/717,132

(22) Filed: Mar. 4, 2010

(65) Prior Publication Data

US 2011/0218561 A1 Sep. 8, 2011

(51) Int. Cl.
*A61C 8/00* (2006.01)
*A61C 5/00* (2006.01)
(52) U.S. Cl. .................. 433/173; 433/174; 433/215
(58) Field of Classification Search .......... 433/172–176, 433/201.1, 215, 218; 606/86 R, 279, 281, 606/190, 164.01, 164.05, 164.08, 164.09, 606/164.1, 164.11, 165.01, 165.02, 165.04, 606/167, 170, 185; 623/16.11, 908, 75, 329, 623/99, 104, 17.11–17.17
See application file for complete search history.

(56) References Cited

U.S. PATENT DOCUMENTS

| | | | | |
|---|---|---|---|---|
| 4,325,373 A | * | 4/1982 | Slivenko et al. | 606/96 |
| 4,521,192 A | * | 6/1985 | Linkow | 433/173 |
| 6,171,312 B1 | * | 1/2001 | Beaty | 606/80 |
| 6,887,077 B2 | * | 5/2005 | Porter et al. | 433/174 |
| 2006/0025797 A1 | * | 2/2006 | Lock et al. | 606/191 |

FOREIGN PATENT DOCUMENTS

| | | |
|---|---|---|
| JP | 2006-247561 | 12/2007 |
| JP | 2006-211063 | 3/2009 |

* cited by examiner

*Primary Examiner* — Todd Manahan
*Assistant Examiner* — Yogesh Patel
(74) *Attorney, Agent, or Firm* — Hiroe & Associates; Dwayne L. Bentley

(57) ABSTRACT

The present invention relates to a method of inserting an implant in a bone. In the bone, a thin slit is formed by a cutting tool in a mesiodistal direction around an insertion spot of the implant. The thin slit is cut and widened by a bone chisel. Into the implant insertion spot, a tool for forming cavity provided with a needle portion is squeezed while being rotated, and a cavity is formed. In the formed cavity and the slit, blood of a patient is collected, by which a tissue is rapidly regenerated and bonded to the inserted implant, and the implant is firmly fixed to the bone.

11 Claims, 12 Drawing Sheets

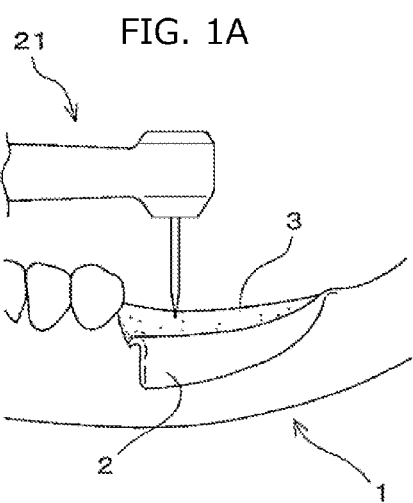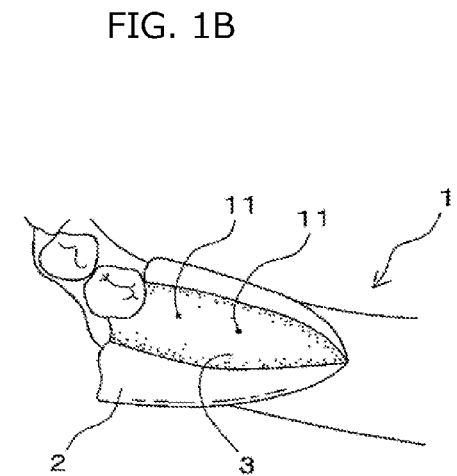

FIG. 6A
FIG. 6B
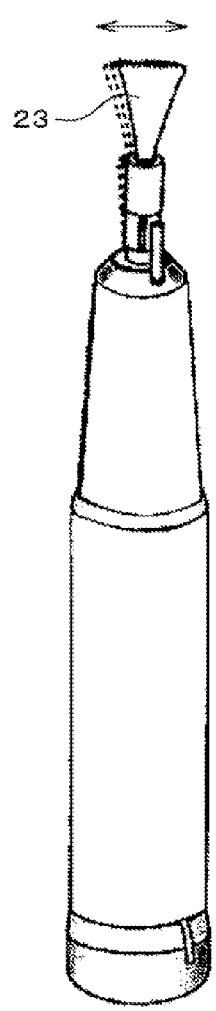
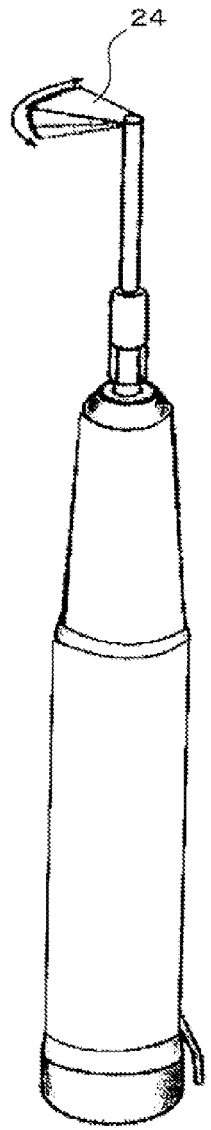

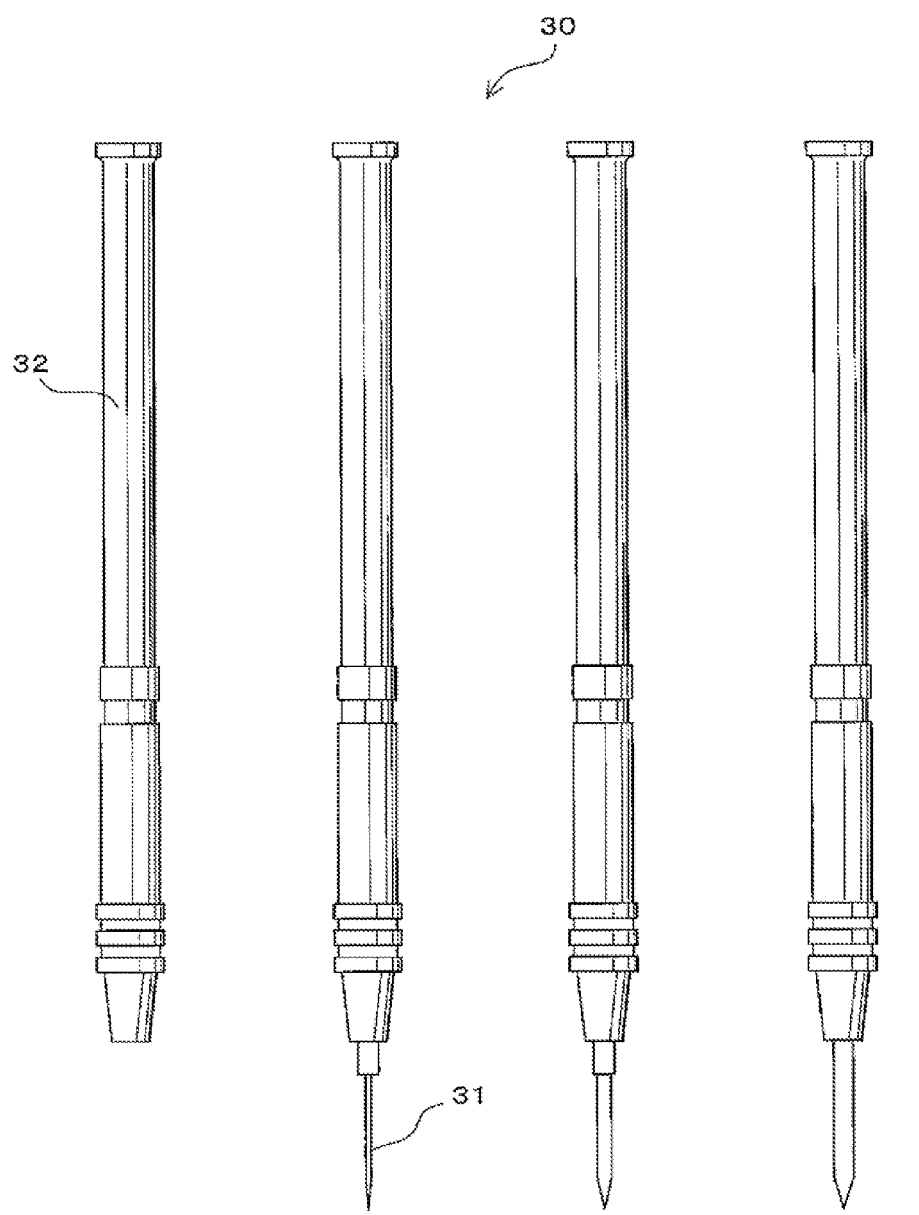

IMPLANT METHOD

BACKGROUND OF THE INVENTION

1. Field of the Invention

The present invention relates to a method for inserting an implant into a living tissue. Particularly, the present invention relates to a method of suitably inserting a dental implant in a jawbone.

2. Description of the Related Art

A procedure to insert an implant in a jawbone will be described using a dental implant treatment as an example. First, a cavity is disposed in a jawbone of a portion where a tooth is missing. Then, in the cavity, an implant (also referred to as an artificial dental root or implant fixture) is inserted. Then, at an end portion of the implant in a state adhering to the jawbone, abutment is attached. Moreover, a super-structural prosthesis (artificial tooth) such as ceramic crown is fixed on the abutment, and the treatment is completed.

In the past, a drill for chipping a jawbone has been widely used as a tool for providing a cavity. Also, a bone chisel forming a cavity by being hammered in has been widely used. However, there are several problems in the method of forming the cavity using these tools. The first problem is that if a cavity is to be formed using these tools, full cure requires a couple of months, and that is a great burden on a patient. The second problem is that if a bone at a portion where the cavity is to be formed is thin or fragile, an implant surgery itself is impossible.

As a method for performing an implant treatment for a thin bone or a fragile bone, bone grafting can be performed. In the bone grafting, a block-state bone sampled from an iliac bone (hip bone) or the like is grafted at a portion of the bone where the implant treatment is to be performed, and the bone is fixed by a screw, a pin and the like to prevent it from moving. After the bone grafting, when a bone tissue is grown to sufficient height and width, a cavity for the implant treatment is formed. However, the bone grafting methods also have many problems. First, an operation to take out a bone is required, and operation spots are increased, which increases a burden on a patient. Secondly, since an extremely long time is required till the bone is grown after the bone grafting, there is a problem that a period till cure is much longer in addition to a period for a usual implant treatment. Thirdly, there is a problem that because of immunity reaction from the bone tissue around the implant portion, the implanted bone might not adhere.

The inventor discloses a plurality of auxiliary tools used in an implant treatment in Japanese Patent Application No. 2006-247561. As these auxiliary tools, auxiliary tools provided with needle portions having various diameters of 0.3 mm or more and 1.4 mm or less, respectively, are disclosed. These auxiliary tools are used in a pretreatment for forming a cavity in which an implant is to be inserted. In the auxiliary tools described in Japanese Patent Application No. 2006-247561, first, the auxiliary tool with the thinnest needle portion is used. When the auxiliary tool with the thinnest needle portion is manually squeezed into a jawbone, a small cavity is formed. After that, by sequentially squeezing the auxiliary tools with thicker needle portions into the same spot in the jawbone, the diameter of the cavity can be gradually increased. By sequentially using the plurality of auxiliary tools, the pretreatment to form a cavity for implant provided with an intended diameter is eventually completed.

The method for forming a cavity in which an implant is to be inserted using the above auxiliary tool can reduce a burden on a patient since an impact applied to the jawbone of the patient is smaller as compared with the prior-art method using a drill or a method of hammering a bone chisel into the bone of the patient.

Also, the inventor discloses an implant provided with an oval sectional shape to be suitably inserted in a thin jawbone in Japanese Patent Application No. 2007-211063 published on Mar. 5, 2009. In Japanese Patent Application No. 2007-211063, a bone chisel suitably used to insert the oval implant is disclosed. This bone chisel has a thickness of a blade edge at 0.3 to 6.0 mm. This bone chisel has a perpendicular sectional shape of the blade edge in an arc shape toward the distal end of the blade edge.

The method using the above bone chisel can further reduce the burden on the patient since the impact applied on the patient's bone is smaller as compared with the prior-art method using a drill or the method of hammering in a bone chisel into the bone of the patient. However, only by using the above auxiliary tool or bone chisel, it is difficult to create a suitable cavity in which a widely used columnar implant is inserted. Thus, a method of inserting an implant with higher versatility and a smaller burden on a patient is in demand.

SUMMARY OF THE INVENTION

An object of the present invention is to provide a method, which can be also applied to a thin bone or a fragile bone, in which an implant could not be inserted. Another object of the present invention is to provide a method of fixing an implant in a short period.

According to an embodiment, a method of inserting an implant of the present invention is provided with a process of determining an insertion spot of the implant in a bone, a process of forming a thin slit with a cutting tool in a mesio-distal direction of the bone around an insertion spot of the implant, a process of widening a width of the slit by inserting a bone chisel into the slit and pushing open an interval between bones on the both sides of the slit, a process of forming a cavity with a small diameter by inserting a tool for forming cavity provided with a thin needle portion into an insertion spot of the implant and squeezing it into the bone while rotating the needle portion, a process of expanding the diameter of the cavity by inserting a tool for forming cavity provided with a needle portion thicker than the diameter of the cavity into the cavity and by squeezing it into the bone while rotating the thicker needle portion, a process of further expanding the diameter of the cavity using a plurality of cavity forming tools provided with larger diameters by repeating the process of expanding the diameter of the cavity, and a process of inserting the implant into the cavity thus formed.

According to the embodiment, with the method of inserting the implant of the present invention, blood of the patient is filled in the formed cavity and the slit. Inside the cavity and the slit filled with the blood, reproduction of the bone progresses extremely rapidly. As a result, the cavity and the slit are rapidly filled and bonded with the inserted implant. The inserted implant is firmly fixed to the bone rapidly.

According to the embodiment, the cutting tool for forming the slit is preferably any one of a diamond bar, a micro saw, a rotating diamond saw or an ultrasonic cutting tool.

According to the embodiment, the bone chisel for widening the slit width is preferably provided with a substantially trapezoidal shaped blade and a side blade is preferably formed on a side face of the blade.

According to the embodiment, the tool for forming cavity preferably has diameters of the needle portions different by 0.2 mm each, and the tool is preferably provided in plural with diameters of 0.3 mm or more and 5.2 mm or less.

A method of inserting an implant according to another embodiment is provided with a process of determining an insertion spot for an implant in a bone, a process of forming a pin hole with a small diameter at the implant insertion spot, a process for forming a narrow slit with a cutting tool in a mesiodistal direction of the bone around the implant insertion spot where the pin hole is formed, a process of widening a width of the slit by pushing open an interval between bones on the both sides of the slit by inserting a bone chisel in the slit, a process of forming a cavity with a small diameter by inserting a tool for forming cavity provided with a thin needle portion in the implant insertion spot and squeezing the needle portion into the bone while rotating it, a process of expanding a diameter of the cavity by inserting a tool for forming cavity provided with a needle portion thicker than the diameter of the cavity into the cavity and squeezing the thicker needle portion into the bone while rotating it, a process of further expanding the diameter of the cavity by repeating the process of expanding the diameter of the cavity using a tool for forming cavity with a larger diameter, and a process of inserting the implant in the formed cavity.

According to the embodiment, a tool for forming a pin hole is preferably a long-neck round bar.

In the method of inserting an implant of the present invention, a slit is provided in a mesiodistal direction so as to communicate with the cavity formed at an implant insertion position. An abundant quantity of blood is supplied to the formed slit and the cavity from the peripheral bones. Since the slit and the cavity are surrounded in all the four directions of its peripheral edges by wall faces of the bone, blood clots can be easily maintained. As a result, the jawbone is regenerated extremely rapidly, and the inserted implant is fixed promptly.

The bone chisel used in the present invention further expands the slit width by widening the interval between the bones on the both sides of the slit disposed in the bone. The tool for forming cavity used in the present invention forms a small cavity and gradually expands the diameter of the cavity by pushing open the bone on the wall face to the periphery so as to form a cavity into which the implant can be inserted. The method using the bone chisel and the tool for forming cavity of the present invention is capable of leaving a wall of bone with a sufficient thickness around the cavity even if the thickness of the bone on the portion where the implant is to be inserted is smaller than the diameter of the implant. As a result, even in a bone where an implant could not be inserted due to lack of bone thickness with the prior-art method of forming a cavity with a drill, an implant can be inserted.

As mentioned above, any of the cutting tool, the bone chisel, and the tool for forming cavity used in the present invention rarely chip the bone. Thus, as compared with the prior-art methods, invasion is less and a patients' pain is smaller.

BRIEF DESCRIPTION OF THE DRAWING

FIG. 1A is a side view of a jawbone 1 in which a pin hole 11 with a small diameter is formed at an insertion spot of an implant, and FIG. 1B is a perspective view of the jawbone 1 where the pin hole 11 is formed;

FIGS. 6A and 6B are perspective views of another example of a cutting tool for forming a thin slit in a jawbone, in which FIG. 6A is a reciprocating micro saw and FIG. 6B is an oscillating micro saw;

FIG. 7A is a sagittal of the micro saw, and FIG. 7B is a perspective view of a diamond saw disk.

FIGS. 8A and 8B show an ultrasonic cutting tool, which is another example for forming a thin slit in a jawbone, in which FIG. 8A is an entire view of the cutting tool, and FIG. 8B is a view illustrating a distal end portion of the cutting tool;

FIGS. 9A and 9B show an example of a bone chisel for expanding a width of a slit, in which FIG. 9A shows a bone chisel for back teeth, and FIG. 9B is a bone chisel for front teeth;

FIGS. 10A-10D are side views of a main body portion of the tool for forming cavity and a plurality of needle portions with different diameters attached to the main body portion;

DETAILED DESCRIPTION OF THE PREFERRED EMBODIMENTS

Figure 2A:
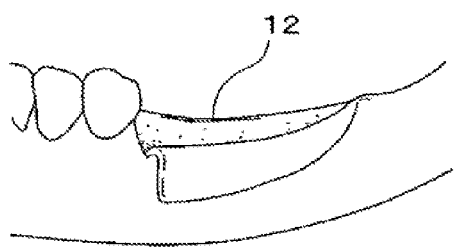
FIG. 2A is a side view of the jawbone 1 in which a thin slit 12 is formed in a mesiodistal direction around the insertion spot of the implant.

A method of inserting an implant according to the present invention will be described below in detail using an example in which the method is applied to a method of inserting a dental implant 40 in a jawbone 1. The dental implant 40 to be embedded into the jawbone 1 is made of titanium and is formed in a substantially cylindrical shape with an entire length of 6.0 to 25.0 mm and the maximum diameter of an in-bone inserted portion is 3.0 to 7.0 mm.

In a preferred embodiment, if an insertion spot of the implant 40 is determined, a mucous 2 of that portion is dissected so as to expose a cortical bone 3. Then, in the insertion spot of the implant 40, a pin hole 11 with a small diameter is disposed using a long-neck round bar 21. At the long-neck round bar 21, a bar with a blade formed at the distal end and having a small diameter is used. FIG. 1A is a side view of the jawbone 1 in which the pin hole 11 with a small diameter is formed at the insertion spot of the implant 40. FIG. 1B is a perspective view of the jawbone 1 in which the pin hole 11 is formed. A process of forming the pin hole 11 is not indispensable for inserting the implant 40 but is performed selectively. The formation of the pin hole 11 has an effect to facilitate positioning of the insertion spot in performing the subsequent processes.

Figure 2B:
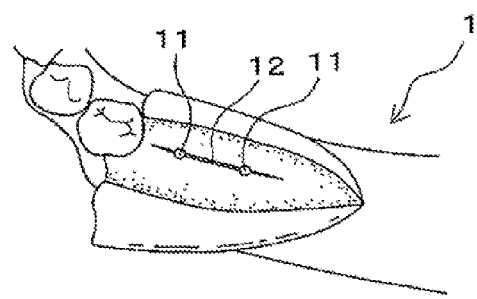
FIG. 2B is a perspective view of the jawbone 1 in which the thin slit 12 is formed.
Figure 5:
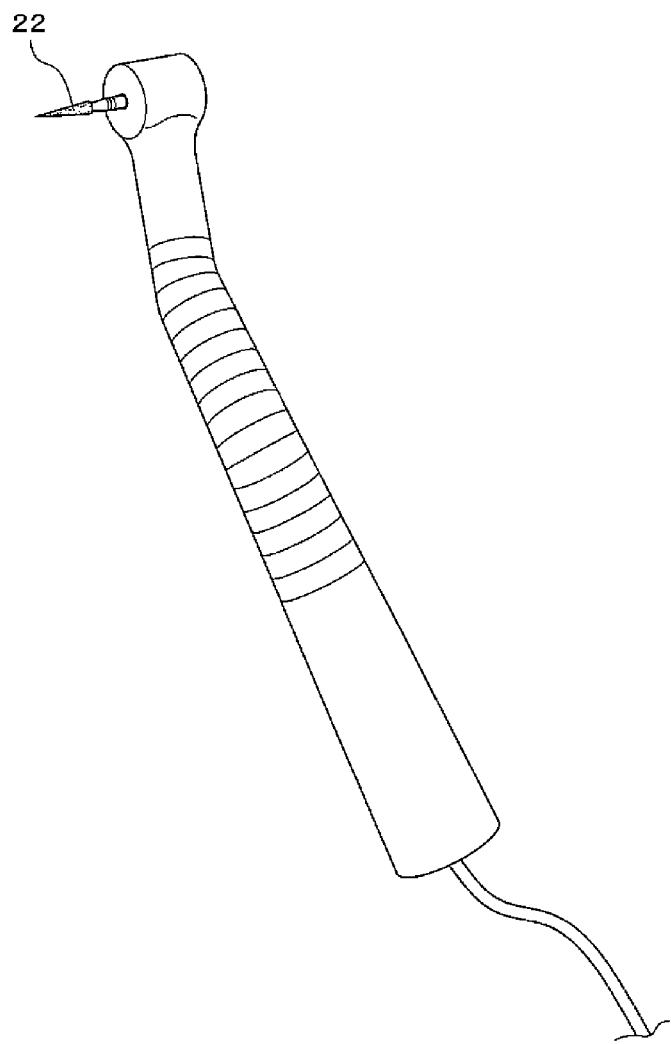
FIG. 5 is a perspective view of a diamond bar, which is an example of a cutting tool for forming a thin slit in a jawbone.
Figure 7A:
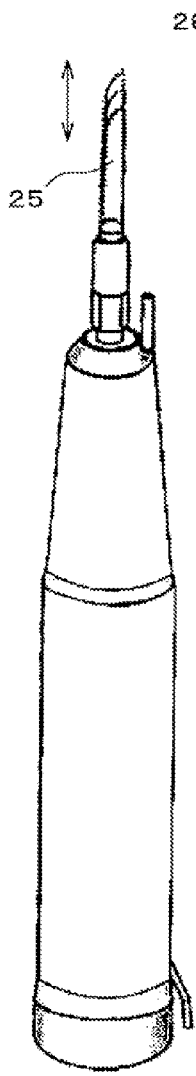
FIGS. 7A and 7B are perspective views of another example of a cutting tool for forming a thin slit in a jawbone.
Figure 7B:
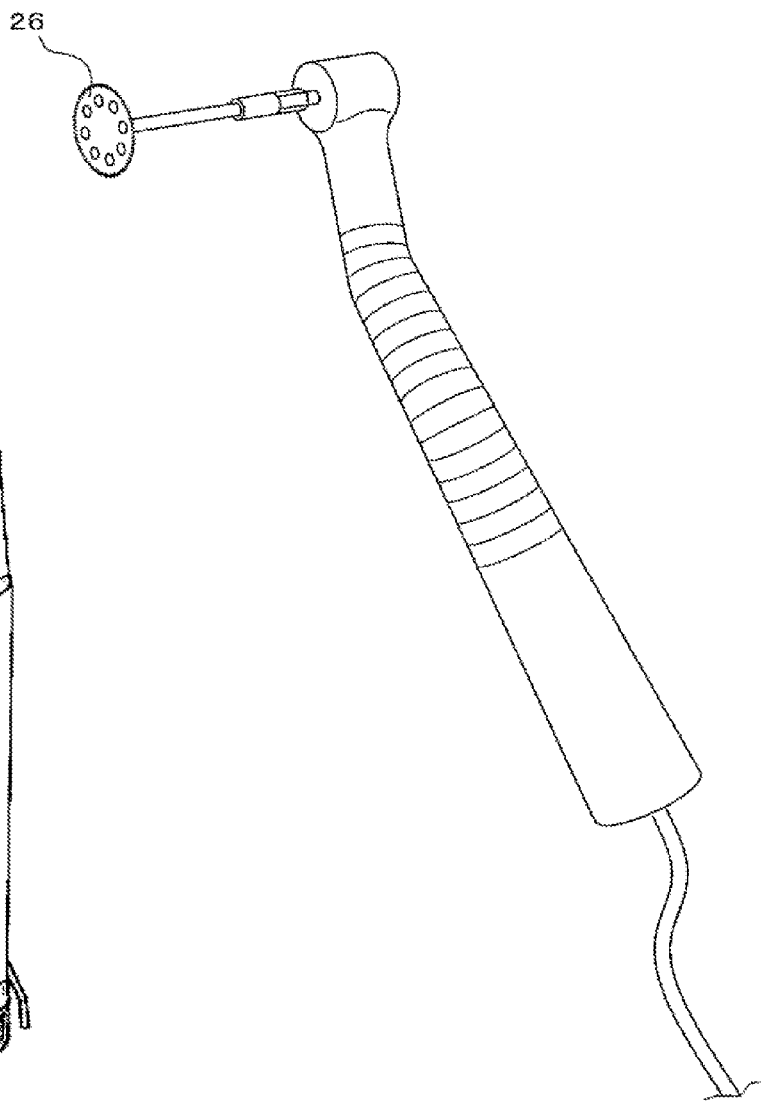
Figure 8A:
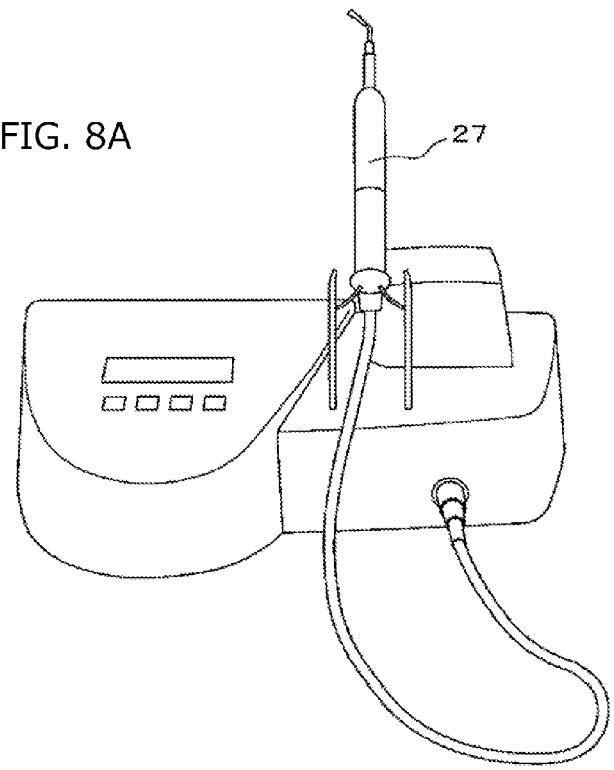
Figure 8B:
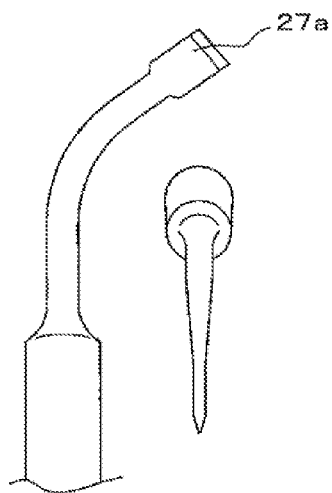

In the preferred embodiment, a thin slit is formed by a cutting tool in the cortical bone 3 around the insertion spot of the implant 40. FIGS. 2A and 2B show the jawbone 1 in which the thin slit 12 is formed in a mesiodistal direction around the pin hole 11 disposed in the insertion spot of the implant 40. A position where the implant 40 is to be inserted becomes a bone crest portion of the jawbone 1 in many cases. Thus, the thin slit 12 is disposed in the mesiodistal direction of the bone crest portion in general. A typical example of the cutting tool for forming the thin slit 12 is a diamond bar 22 shown in FIG. 5. Also, an implant motor in which a drill portion is replaced by a diamond thin bar can be used as an alternative. Moreover, a reciprocating micro saw 23 shown in FIG. 6A, a oscillating micro saw 24 shown in FIG. 6B, a sagittal micro saw 25 shown in FIG. 7A or a rotating diamond saw disk 26 shown in FIG. 7B can be used as an alternative. Also, an ultrasonic cutting tool 27 shown in FIGS. 8A and 8B can be used as an alternative. A device shown in FIG. 8A is a piezo surgery (PIEZOSURGERY, registered trademark) of the ultrasonic cutting tool 27. A device shown in FIG. 8B is a partially enlarged view of a distal end portion 27a of the ultrasonic cutting tool 27.

Subsequently, by using a bone chisel, an interval between a cortical bone 3a and a cortical bone 3b on the both sides of the slit 12 is pushed open, and the slit 12 reaches a cancellous bone under the cortical bone 3. An operator can make an incision in the cancellous bone at a bottom part of the slit 12 by inserting a blade edge into the thin slit 12 while holding a handle portion of a bone chisel 28 or a bone chisel 29 by fingers. A width of the slit 12 is expanded, and a slit 13 with a larger width is formed.

Figure 3A:
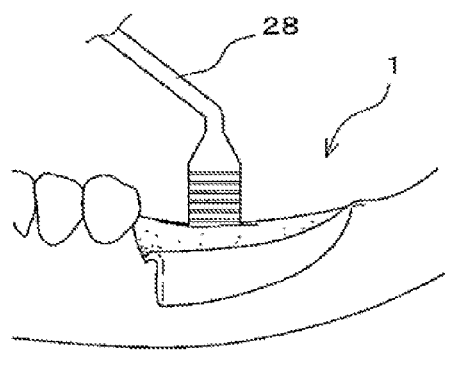
FIG. 3A is a side view of the jawbone 1 having a slit 13 whose width is expanded.
Figure 3B:
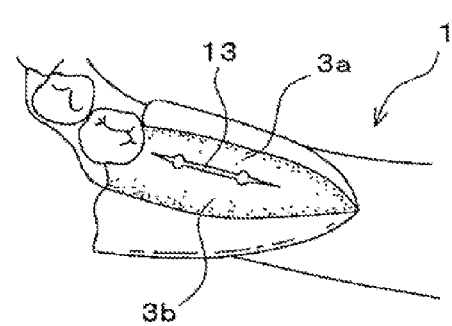
FIG. 3B is a perspective view of the jawbone 1 having the slit 13 whose width is expanded.
Figure 9A:
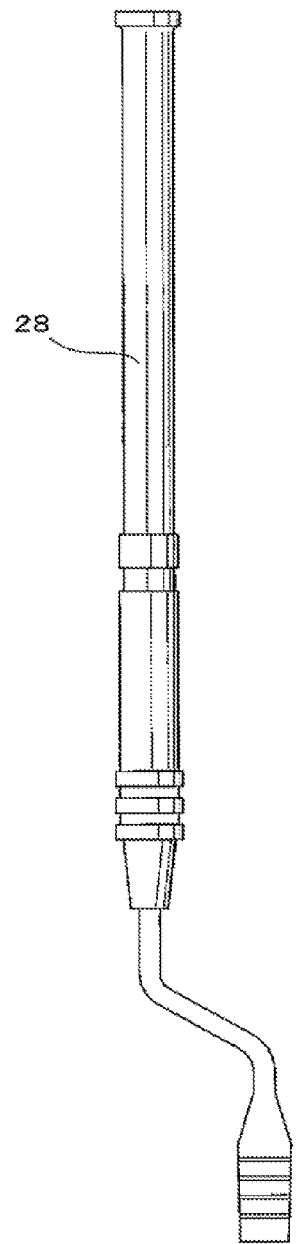
Figure 9B:
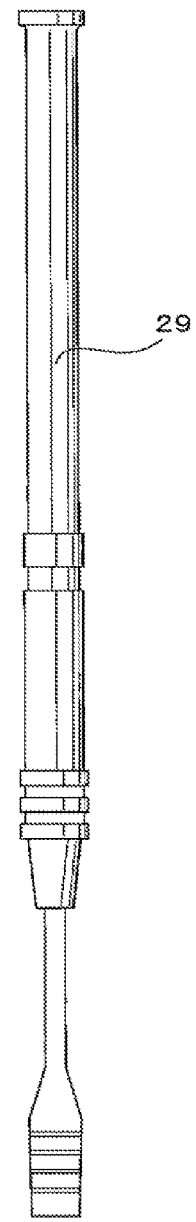

FIGS. 3A and 3B show the jawbone 1 in which the slit 13 with a large width is formed between the cortical bone 3a and the cortical bone 3b. FIGS. 9A and 9B show an OAM bone slitter by Medical Apex Co., Ltd., which is a bone chisel suitably used in a process of forming the slit 13. FIG. 9A shows a bone chisel 28 for back teeth, and FIG. 9B shows a bone chisel 29 for front teeth. As shown in FIGS. 9A and 9B, the bone chisels 28 and 29 are provided with working end portions including a blade formed substantially in a rectangular shape. Also, the bone chisels 28 and 29 preferably have side blades formed on both sides of the blade edge. By means of the side blades, the length of the slit 13 is expanded extremely easily.

The shape of the bone chisels 28 and 29 and a method of use will be described in more detail. The bone chisels 28 and 29 are bone chisels that can properly form a cavity into which an implant is inserted in a thin jawbone. The bone chisel 28 has a blade in a substantially trapezoidal flat plate shape, and the working end portion including the blade edge is bent with respect to a handle (main body portion). The bone chisel 29 has a blade in a substantially trapezoidal flat plate shape and is formed in a straight line state from the handle to the blade edge. The bone chisels 28 and 29 have an arc cross sectional shape of the blade edge toward the top of the tip end of the blade edge. Also, the bone chisels 28 and 29 have a blade-edge thickness of 0.3 to 6.0 mm or more preferably of 0.5 to 3.0 mm. The blade-edge thickness here means a thickness from the end of the arc of the blade edge and the other face. Also, the shape of the cross section of the blade edge refers to the sectional shape of a face perpendicular to the trapezoidal flat plate face and the blade edge line. A radius of the arc of the blade edge is larger than the blade edge thickness and 0.3 mm or more.

The shape of the blade edge of the bone chisels 28 and 29 is preferably a one-side blade having a flat face on one side and an arc shape on the other face. In principle, during an operation, the flat face of the blade is supposed to be brought into contact with the tongue side or the palate side of the jawbone and the arc-shaped face with the cheek side. That is because the bone on the tongue side or the palate side is hard but is easily broken, and the arc-shaped face with an action to push out the jawbone is not suitable to be brought into contact. The one-side blade of the bone chisels 28 and 29 has an angle formed between the flat face and a tangent line of the arc-shaped face of the blade preferably at 20 to 40° or most preferably at substantially 30°. Being provided with the arc-shaped face, the bone chisel has an action to push out the jawbone to the periphery instead of chipping and/or hollowing out a material as in the case of the prior-art bone chisel, and the stood blade is rarely dulled. As a result, an operation can be performed even in a thin jawbone without lowering its strength.

As shown in FIG. 9A, the bone chisel 28 has the working end portion including the blade edge bent with respect to the handle and the blade is formed substantially on the same plane with a virtual plane including the handle and the working end portion. Since the working end portion including the blade edge of the bone chisel 28 is bent, as shown in FIG. 3A, the slit 13 can be formed without the mouth of a patient wide open during the operation of the back teeth, and mental and physical burdens on the patient can be alleviated. Also, since the blade is formed in a specific direction with respect to the handle as above, a force can be easily applied in the mesiodistal direction through the handle with which the operator grasps the bone chisel when the slit 13 is to be formed. As a result, the operation can be performed safely and with good operability.

The bone chisels 28 and 29 are characterized in that they have a substantially trapezoidal flat plate shape like a chisel and a sharper distal end, which is different from a prior-art bone chisel with a blade edge to be hammered in. The prior-art bone chisel is intended to split or chip the bone, but the present invention is characterized by forming the slit 13 by cutting into the jawbone. The operator pushes in the blade edge while pressing the substantially trapezoidal flat plate blade perpendicularly to the jawbone at a position in the mesiodistal direction along a tooth row. As a result, a straight slit is formed. Since the blade-edge sectional shape of the bone chisels 28 and 29 is an arc shape toward the top of the tip end of the blade edge, it is convenient to push open a linear opening portion widely while the blade edge advances.

As a preferred embodiment, the bone chisels 28 and 29 preferably have a side blade formed on a diagonal side portion of the trapezoidal flat plate shaped blade by forming an arc shape with the sectional shape in the horizontal direction of the working end portion toward the both sides. The sectional shape in the horizontal direction of the blade portion here means a plane in parallel with the blade edge and corresponds to the cross section with respect to the side blade. The side blade of the bone chisels 28 and 29 facilitates extension of the slit 13 along the jawbone.

Figure 4A:
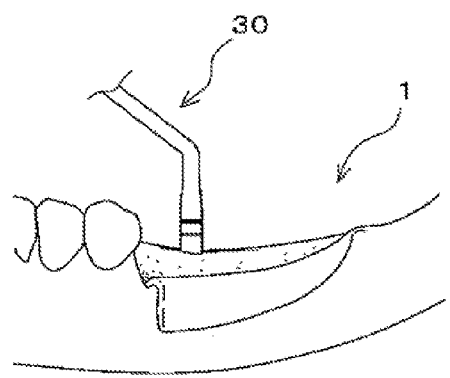
FIG. 4A is a side view of the jawbone 1 into which a needle portion 31 of a tool 30 for forming cavity is squeezed at the insertion spot of the implant.
Figure 4B:
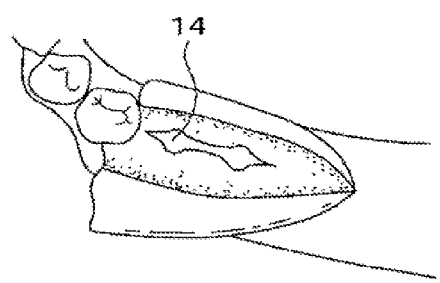
FIG. 4B is a perspective view of the jawbone where a cavity 14 is formed.

Subsequently, the operator inserts the tool 30 for forming cavity into the insertion spot of the implant 40 and forms a cavity 14 by squeezing a needle portion 31 into the bone while manually rotating it. FIG. 4A shows a side view of the jawbone 1 into which the tool 30 for forming cavity is inserted, and FIG. 4B shows the jawbone 1 in which the small cavity 14 is formed at the center part of the slit 13.

FIGS. 10A-10D show an AUGMETER by Medical Apex Co., Ltd., which is the tool 30 for forming cavity suitably used in a process for forming the cavity 14. The tool 30 for forming cavity is provided with the needle portion 31 and a main body portion 32. The needle portion 31 is formed by metal and firmly screwed to the main body portion 34. FIGS. 10A-10D show examples of the tool 30 for forming cavity provided with the thin needle portion 31 (see FIG. 10B), the one provided with the relatively thick needle portion 31 (see FIG. 10C), and the one provided with the thickest needle portion 31 (see FIG. 10D). The diameters of the needle portions 31 are formed so as to become 0.3 mm or more and 5.2 mm or less.

Usually, a set with 10 to 30 pieces of the tool 30 for forming cavity with the diameters of the needle portions different by 0.2 mm is prepared. The operator makes a choice according to the depth and diameter of the cavity to be formed in the set.

The tool 30 for forming cavity shown in FIGS. 10A-10D is a tool mainly used for front teeth, and the main body portion 32 is formed straight. On the other hand, for forming the cavity 14 in the back tooth portion, the one with the needle portion side of the main body portion 32 bent as shown in FIG. 4A is used. The tool 30 for forming cavity for back tooth enables insertion of the needle portion 31 into the insertion spot of the implant 40 without having a patient open the mouth wide in an operation.

For formation of the cavity 14, first, the tool 30 for forming cavity having the thin needle portion 31 is used. The thin needle portion 31 of the tool 30 for forming cavity is inserted by the operator into a cancellous bone 4 corresponding to the insertion spot of the implant 40. The operator squeezes the needle portion 31 into the cancellous bone while manually rotating it by approximately 30 degrees right and left while supporting the main body portion 32 of the tool 30 for forming cavity with the hand. Since the cortical bone 3 and the cancellous bone 4 are pushed open to outside of the cavity 14 by the tool 30 for forming cavity having the thin needle portion 31, the cavity 14 provided with a required depth is formed. During this period, the operator can adjust the force to squeeze in the tool 30 for forming cavity by checking hardness of the bone transmitted to the fingers through the tool 30 for forming cavity. Even if the jawbone 1 is fragile and soft, the appropriate cavity 14 can be formed without breaking the jawbone 1.

Figure 11:
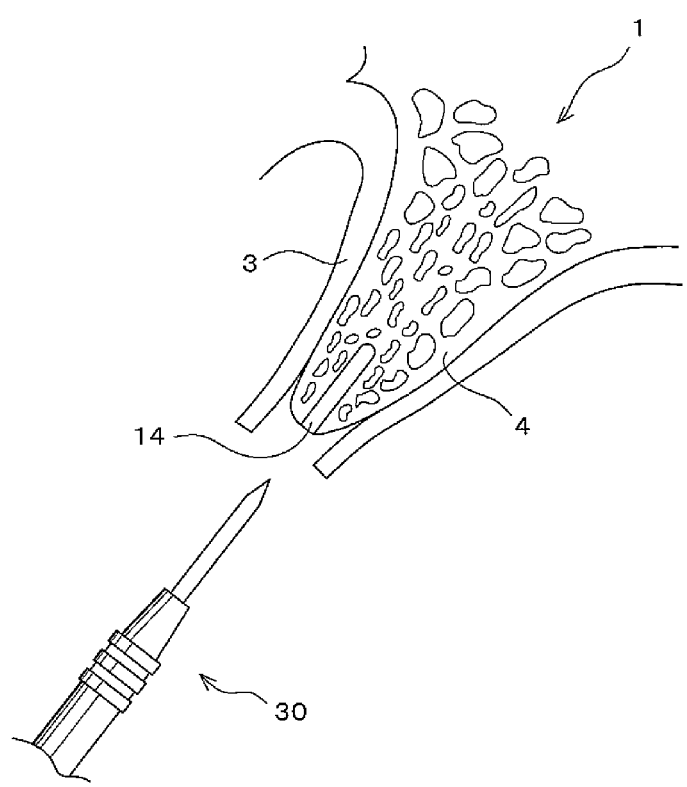
FIG. 11 is a sectional view of a jawbone in which an expanded cavity is formed at an insertion spot of an implant by the tool for forming cavity.

Subsequently, the operator selects the tool 30 for forming cavity provided with the thicker needle portion 31 and inserts it into the cavity 14. Then, by holding the main body portion 32 by hand and rotating it, the operator squeezes the needle portion 31 of the tool 30 for forming cavity into the bone. By means of a motion of the needle portion 31, the cortical bone 3 and the cancellous bone 4 located at the position of the cavity 14 are pushed open to the outside, and the diameter of the cavity 14 is expanded. The operator can further expand the diameter of the cavity 14 by repeating the process of squeezing the tool 30 for forming cavity provided with the thicker needle portion 31. FIG. 11 shows a partial sectional view of the jawbone 1 in which the cavity 14 having a diameter into which the implant 40 can be inserted is formed by the tool 30 for forming cavity with a larger diameter being squeezed into.

Figure 12:
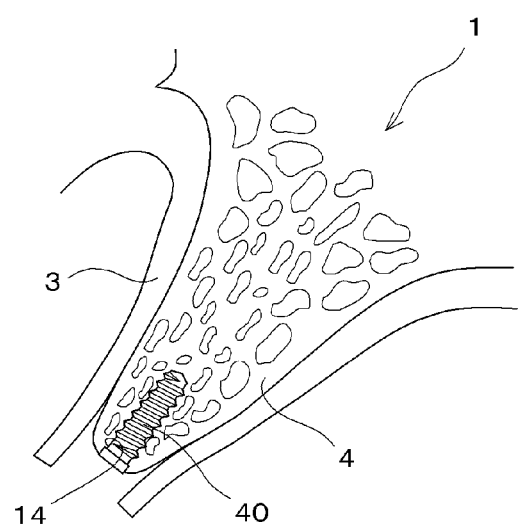
FIG. 12 is a sectional view of the jawbone in which the implant is inserted.

FIG. 12 is a partial sectional view illustrating a state in which the implant 40 is inserted into the cavity 14 formed in the jawbone 1. After the formation of the cavity 14 has progressed, the tissue of the jawbone 1 temporarily pushed open to the periphery is moved to return to the original position when the implant 40 is inserted. The tissue of the jawbone having moved to the original position can firmly bond to the implant 40, and stable initial fixation of the implant 40 is accomplished.

Referring to FIGS. 3B and 4B again, the slit 13 formed by the bone chisels 28 and 29 and the cavity 14 formed by the tool 30 for forming cavity receive abundant supply of blood from the peripheral jawbone 1. Moreover, since the slit 13 and the cavity 14 are surrounded in all the four directions of its peripheral edges by wall faces of the jawbone, blood clots can be easily maintained without flowing out. As a result, the jawbone is regenerated extremely rapidly, and secondary fixation of the inserted implant 40 is accomplished firmly.

EXAMPLE

An example of a method to which the method of inserting an implant of the present invention is applied will be shown below. A patient was a 44-year-old female, and the method of the present invention was applied to the front teeth portion of the upper jawbone. A bone width of the upper jawbone of the patient was approximately 1.2 mm. An implant with the diameter of approximately 3.7 mm and a length of approximately 13 mm was inserted therein. First, a pin hole was disposed at a spot in the upper jawbone where the implant is to be inserted by the long-neck round bar 21. Then, using the diamond bar, a thin slit was formed in the mesiodistal direction slightly on the palate side of the upper jawbone around this pin hole. By disposing the slit slightly on the palate side, more alveolar bone could be left on the lip side. Then, a bone slitter was inserted into the slit so as to push open the interval between bones on the both sides of the slit. Then, into the spot where the implant is to be inserted, an AUGMETER provided with a needle portion with the diameter of 0.5 mm was inserted, and the needle portion was squeezed into the bone while being rotated so as to form a cavity with a small diameter. Moreover, AUGMETER having thicker needle portions was sequentially used, and the diameter of the cavity was expanded. In the end, the cavity with the diameter of 3.2 mm and the depth of 13 mm could be formed. Then, the implant was inserted into this cavity. During this work, devulsion of the jawbone did not occur at all, and a bone thickness sufficient to support the implant could be left around the cavity on both the palate side and the lip side. Moreover, this treatment required only approximately 1.5 hours from the formation of the pin hole to the insertion of the implant, and the implant could be inserted extremely rapidly. At the same time as the insertion, the jawbone having been pushed open once returned to the original position to be brought into close contact with the implant body, by which firm initial fixation could be obtained. Moreover, after the treatment, blood is supplied to the formed cavity and the slit, and the tissue of the jawbone was regenerated rapidly. As a result, the inserted implant was kept in a state firmly fixed in the cavity semipermanently.

A specific mode of the present invention was described in detail on the basis of the embodiments, but they are only exemplifications and do not limit the scope of the claims. The technique described in the claims includes various deformation and changes of the above exemplified specific examples.

What is claimed is:

1. A method of inserting an implant, comprising:
   determining an insertion spot of the implant in a bone;
   forming a thin slit in the bone with a cutting tool in a mesiodistal direction of the bone around the implant insertion spot;
   widening a width of the slit by opening an interval in the bone by inserting a bone chisel in the slit;
   within said slit, forming a cavity having a first diameter by inserting a cavity forming tool having a thin needle portion in the implant insertion spot and pushing and rotating the needle portion into the bone;
   expanding the first diameter of the cavity by inserting the cavity forming tool having a thicker needle portion into the cavity and pushing and rotating the thicker needle portion into the bone;
   further expanding the first diameter of the cavity by repeating the insertion of the cavity forming tool into the cavity and pushing and rotating the tool, wherein the repeated insertion utilizes a progressively thicker needle portion, and wherein the repeated insertion, pushing, and rotating create larger diameters; and
   inserting the implant in the cavity having the larger diameter, wherein a patient's blood remains in the cavity and in the slit, and wherein due to the remaining blood, the bone surrounding the cavity and the slit is rapidly regenerated and bonded to the inserted implant, and wherein the inserted implant is firmly fixed to the bone.

2. The method of inserting an implant according to claim 1, wherein the cutting tool for forming the slit is any one of a diamond bar, a micro saw, a rotating diamond saw or an ultrasonic cutting tool.

3. The method of inserting an implant according to claim 1, wherein the bone chisel for expanding the width of the slit is provided with a substantially rectangular blade, and a side blade is formed on a side face of the blade.

4. The method of inserting an implant according to claim 1, wherein the cavity forming tools are a plurality of cavity forming tools having diameters of needle portions differing by 0.2 mm, and wherein the diameters range from 0.3 mm to 5.2 mm.

5. The method of inserting an implant according to claim 1, wherein the bone is a jawbone, and wherein the implant is a dental implant.

6. A method of inserting an implant, comprising:
   determining an insertion spot of the implant in a bone;
   forming a pin hole having a small diameter at the implant insertion spot;
   forming a thin slit with a cutting tool in a mesiodistal direction of the bone around the implant insertion spot where the pin hole is formed;
   widening a width of the slit by pushing open an interval in the bone by inserting a bone chisel in the slit;
   within said slit, forming a cavity having a first diameter by inserting a cavity forming tool having a thin needle portion in the implant insertion spot and pushing and rotating the needle portion into the bone;
   expanding a diameter of the cavity by inserting the cavity forming tool having a thicker needle portion into the cavity and pushing and rotating the thicker needle portion into the bone;
   further expanding the first diameter of the cavity by repeating the insertion of the cavity forming tool into the cavity and pushing and rotating the tool, wherein the repeated insertion utilizes a progressively thicker needle portion, and wherein the repeated insertion, pushing, and rotating create larger diameters; and
   inserting the implant in the cavity having the larger diameter, wherein a patient's blood remains in the cavity and in the slit, and wherein due to the remaining blood, the bone surrounding the cavity and the slit is rapidly regenerated and bonded to the inserted implant, and wherein the inserted implant is firmly fixed to the bone.

7. The method of inserting an implant according to claim 6, wherein the tool for forming a pin hole is a long-neck round bar.

8. The method of inserting an implant according to claim 6, wherein the cutting tool for forming the slit is any one of a diamond bar, a micro saw, a rotating diamond saw or an ultrasonic cutting tool.

9. The method of inserting an implant according to claim 6, wherein the bone chisel for expanding the width of the slit is provided with a substantially trapezoidal blade, and a side blade is formed on a side face of the blade.

10. The method of inserting an implant according to claim 6, wherein the cavity forming tool is a plurality of cavity forming tools having diameters of needle portions differing by 0.2 mm, and wherein the diameters range from 0.3 mm to 5.2 mm.

11. The method of inserting an implant according to claim 6, wherein the bone is a jawbone, and the implant is a dental implant.

* * * * *